(12) United States Patent
Stasz et al.

(10) Patent No.: US 6,702,755 B1
(45) Date of Patent: Mar. 9, 2004

(54) SIGNAL PROCESSING CIRCUIT FOR PYRO/PIEZO TRANSDUCER

(75) Inventors: Peter Stasz, St. Paul, MN (US); Terry Hudrlik, Blaine, MN (US)

(73) Assignee: Dymedix, Corp., Minneapolis, MN (US)

( * ) Notice: Subject to any disclaimer, the term of this patent is extended or adjusted under 35 U.S.C. 154(b) by 442 days.

(21) Appl. No.: 09/860,089

(22) Filed: May 17, 2001

(51) Int. Cl.[7] .................................................. A61B 5/08
(52) U.S. Cl. ........................ 600/534; 600/535; 600/536; 600/538
(58) Field of Search ................... 600/534, 532, 600/539, 540, 541, 542, 586, 535, 536, 537, 538; 29/612

(56) References Cited

U.S. PATENT DOCUMENTS

| 5,161,541 A | * 11/1992 | Bowman et al. ............ 600/537 |
| 5,311,875 A | 5/1994 | Stasz .......................... 128/724 |
| 5,331,968 A | 7/1994 | Williams et al. ............ 128/721 |
| 5,558,099 A | * 9/1996 | Bowman et al. ............ 600/538 |
| 5,832,592 A | * 11/1998 | Bowman et al. ............... 29/612 |
| 6,254,545 B1 | * 7/2001 | Stasz et al. .................. 600/537 |
| 6,485,432 B1 | * 11/2002 | Stasz et al. .................. 600/532 |
| 6,491,642 B1 | * 12/2002 | Stasz .......................... 600/537 |
| 6,551,256 B1 | * 4/2003 | Stasz et al. .................. 600/586 |

* cited by examiner

Primary Examiner—Henry Bennett
Assistant Examiner—Fadi H. Dahbour
(74) Attorney, Agent, or Firm—Nikolai & Mersereau, P.A.; Thomas J. Nikolai

(57) ABSTRACT

An adapter for interfacing a pyro/piezo sensor to a polysomnograph machine comprises a differential input amplifier coupled to receive the raw transducer signals from a PVDF film transducer to provide a requisite gain while rejecting common mode noise. The resulting amplified signal is filtered to separate the pyro signal from the piezo signal and the piezo signal is further applied to half-wave rectifier stages that function to remove baseline noise from the piezo signal before its being applied to a microphone channel of an existing PSG machine.

7 Claims, 3 Drawing Sheets

SIGNAL PROCESSING CIRCUIT FOR PYRO/PIEZO TRANSDUCER

BACKGROUND OF THE INVENTION

I. Field of the Invention

This invention relates generally to an electronic signal processing circuit for adapting a pyro/piezo sensor to a conventional polysomnograph machine of the type commonly used in sleep lab applications, and more particularly to an adapter that isolates pyro (breathing-related) signal components of the sensor from piezo (snore-related) signal components and which removes baseline noise from the piezo signal component.

II. Discussion of the Prior Art

In addressing sleep-related problems, such as sleep apnea, insomnia and other physiologic events or conditions occurring during sleep, various hospitals and clinics have established so-called sleep labs where through the use of instrumentation, a patient's sleep patterns can be monitored and recorded for later analysis so that a proper diagnosis and therapy can be arrived at. A variety of sensors have been devised for providing recordable signals related to respiratory patterns during sleep. These sensors commonly are mechanical to electrical transducers that produce an electrical signal related to body movement. For example, in U.S. Pat. No. 5,331,968, the sensor comprises a plethysmograph band adapted to encircle a patient's chest and which produces an electrical signal associated with chest movement due to respiratory activity. Other transducers include infrared pulse oximeters for monitoring blood oxygen levels, and microphones for detecting snoring. In addition, a plurality of electrodes for sensing myopotentials and/or cardiac rhythms are often utilized. These sensors feed their electrical signals into an electronics module referred to as a polysomnograph or PSG machine.

Recently, Dymedix Corporation, applicant's assignee, has introduced a new type of sensor comprising a polyvinylidene fluoride (PVDF) film which is found to exhibit both pyroelectric and piezoelectric properties. Information relating to this type of sensor may be found in the Stasz U.S. Pat. 5,311,875 as well as in copending application Ser. No. 09/416,660, filed Oct. 12, 1999 (now U.S. Pat. No. 6,254,545). PVDF sensors of the type described are adapted to be affixed to a subject's upper lip so that air flow due to inspiration and expiration impinge on the sensor to produce an output signal related to temperature changes occasioned by the inspiratory and expiratory flow. The sensor also is especially designed to pick up sound vibrations due to snoring episodes.

To successfully market this new type of sensor, it is desirable that it be able to be used with existing polysomnograph machines already in place in the sleep labs.

SUMMARY OF THE INVENTION

The present invention provides an adaptor for interfacing a pyro/piezo sensor to a PSG machine. It comprises a differential input amplifier having a pair of input terminals that are adapted to be coupled to the pyro/piezo sensor and an output terminal. The differential input amplifier is configured to significantly attenuate common-mode noise while providing a predetermined gain factor by which the sensor output signal is amplified. The output of the differential input amplifier is fed to a filter circuit that operates to separate a pyro component of the sensor output signal from a piezo component thereof The pyro signal component, which relates to inspiratory and expiratory air flow of the patient, feeds directly into a first channel of the PSG machine. The piezo component of the sensor output signal, which relates to sound or snoring, is first fed through a dead-band circuit which is effective to remove baseline noise from the piezo component of the sensor output signal. In coupling the resulting piezo component, absent its baseline noise, to the PSG sound channel, a differential output driver circuit is interposed.

By utilizing a differential input amplifier with a predetermined gain factor and by appropriately signal processing the amplified PVDF film sensor output signal, the pyro and piezo components thereof can be readily matched to existing PSG electronic boxes already on hand in most sleep labs.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
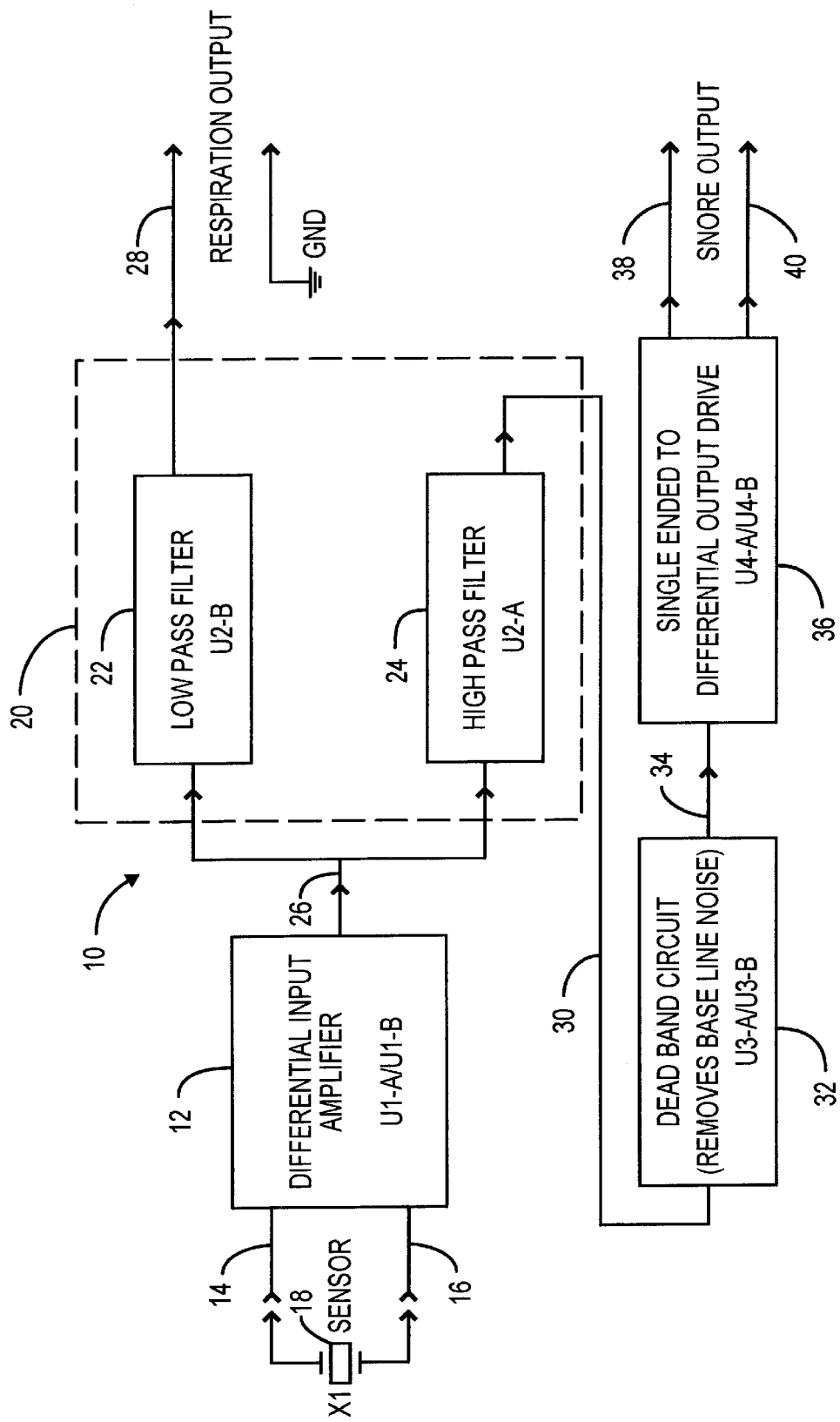
FIG. 1 is a schematic block diagram of the adapter module comprising a preferred embodiment of the present invention.

Referring to FIG. 1, there is indicated generally by numeral 10 the functional components comprising the adapter module of the present invention. It is seen to include a differential input amplifier stage 12 having a pair of input terminals 14-16 to which the leads of a PVDF film transducer 18 are connected. The film transducer 18 is preferably constructed in accordance with the teachings of copending application of Peter Stasz, et al. Ser. No. 09/852,195, filed May 9, 2001 (now U.S. Pat. No. 6,491,642), and entitled "PYRO/PIEZO SENSOR", the teachings of which are hereby incorporated by reference as if filly set forth herein. The sensor 18 is adapted to be placed on a subject's upper lip so that inspiratory and expiratory air flow through the nostrils impinges thereon and also so that the sensor is responsive to vibration due to sound (snoring).

The differential input amplifier 12 comprises an instrumentation-type amplifier which functions to increase the common-mode rejection of the adapter system so as to make it less susceptible to 60 Hz noise present in the environment as well as to motion artifacts. Without limitation, the differential input amplifier may have a gain in the range of from 2 to 10 with about 6.2 being quite adequate.

The output from the amplifier 12 is applied to a filter network shown enclosed by dashed line box 20. It includes a low-pass filter 22 whose cut-off frequency may be about 0.8 Hz and a high-pass filter 24 whose cut-off frequency is about 20 Hz. The filter network 20 that is connected to the output terminal 26 of the differential input amplifier 12 operates to separate a pyro component of the sensor output signal from a piezo component of that sensor output signal. In particular, the low-pass filter 22 is effective to pass the pyro signal relating to respiratory activity directly to an input jack of the PSG machine (not shown) by way of line 28.

The high-pass filter 24 passes the piezo signal component of the transducer 18 over a line 30 to a dead band circuit 32 that is especially configured to remove objectionable baseline noise from the snore signal. The dead band circuit 32 effectively discriminates against signal excursions that do not exceed an upper (positive) and a lower (negative) threshold value. Those excursions exceeding the present reference values are delivered over line 34 to a single-ended to differential output driver circuit 36. It has been found that a differential output across output lines 38 and 40 are more compatible with existing PSG equipment in the field. The differential snore output signal is applied to the "microphone channel" of the conventional PSG machine.

Figure 2:
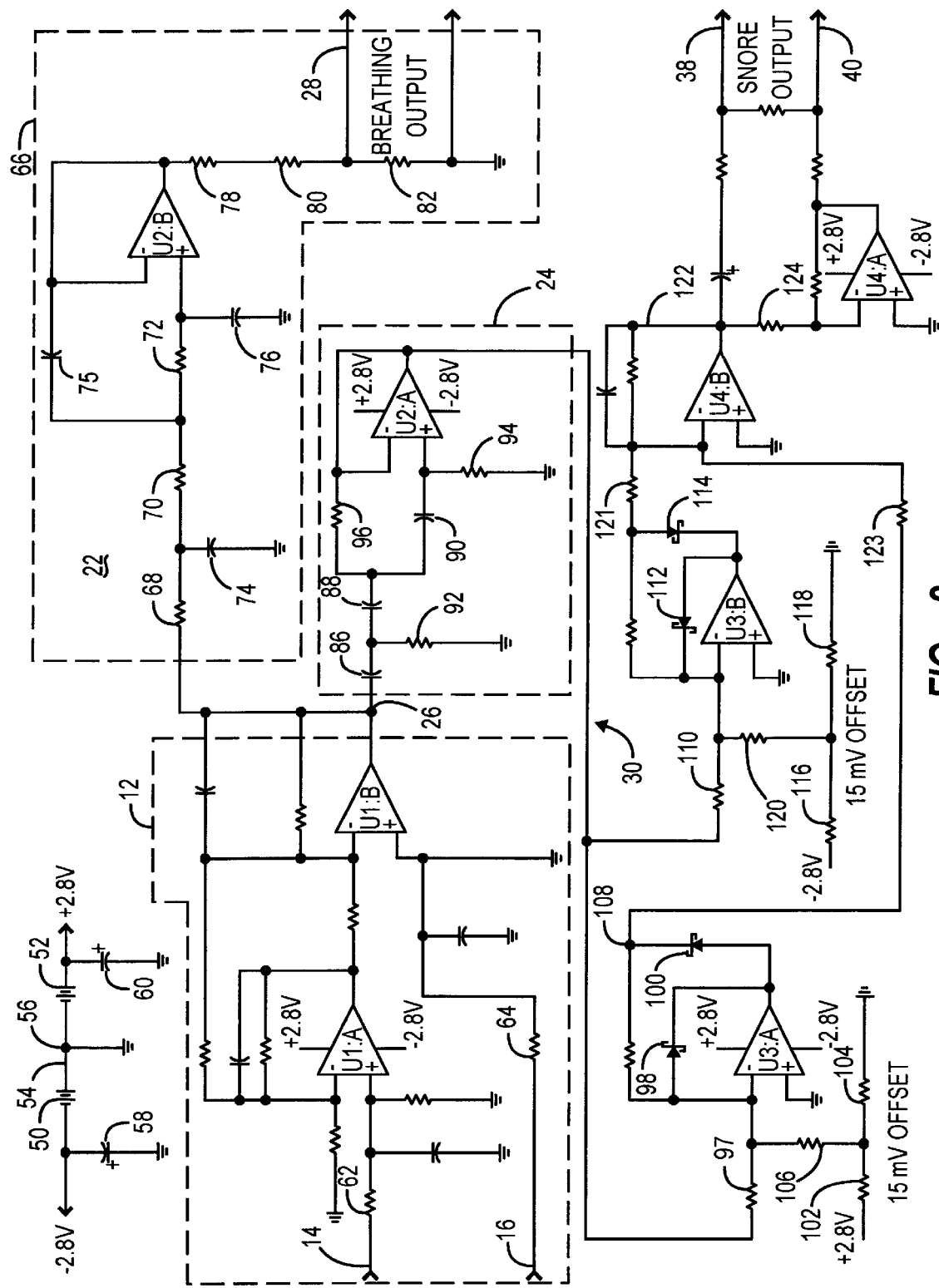
FIG. 2 is an electrical schematic diagram of the preferred embodiment showing a detailed implementation thereof.

Having described the overall configuration of the adapter module with the aid of FIG. 1, a more detailed explanation of a specific implementation of the adapter will now be presented and, in that regard, reference is made to the schematic electrical diagram of FIG. 2. The adapter of the present invention is integral with the cable used to couple the transducer 18 to the polysomnograph machine. As such, it incorporates its own power supply in the form of lithium batteries 50 and 52 which are connected in series by a conductor 54 but with a grounded center tap 56 so that positive and negative reference voltages of about 2.8 volts are available for use by the remainder of the adapter module. Electrolytic capacitors 58 and 60, poled as indicated, are connected in shunt with the lithium cells 50 and 52 and serve to provide AC bypassing of the ±2.8 volt power rails.

The input terminals 14 and 16 to the differential input amplifier are respectively coupled, via resistors 62 and 64, to the non-inverting inputs of operational amplifiers U1-A and U1-B. Those skilled in the art will appreciate that the op amps, configured as shown are typical instrumentation-type amplifiers designed to produce a predetermined gain while rejecting common-mode noise. The output from the differential input amplifier circuit 12 appears at junction 26 and feeds a low-pass filter circuit 22 shown enclosed by the broken line box 66. More particularly, the output appearing at junction 26 is applied, via series connected resistors 68, 70 and 72, to the non-inverting input of an operational amplifier U2-B and those resistors, along with capacitors 74, 75 and 76 cooperate with the operational amplifier U2-B to function as a low-pass filter. A voltage divider including resistors 78, 80 and 82 is used to drop the pyro-based signal component to the acceptable levels of the PSG machine to which the PVDF film transducer is being interfaced. The values of the resistors 68, 70 and 72 and the capacitors 74, 75 and 76 may be set to establish a cut-off frequency of the low-pass filter circuit 22 to about 0.8 Hz as mentioned previously.

The output from the differential input amplifier stage U1-B at junction 26 is applied, via a high-pass filter 24, which comprises an operational amplifier U2-A having its output directly shorted to its inverting input. The cutoff frequency for the high-pass filter stage is established by the component values of capacitors 86, 88 and 90 and the resistors 92, 94 and 96. To provide adequate separation between respiratory (pyro) based signals and piezo (snore-related) signals, a cutoff frequency of about 20 Hz has proven adequate.

The piezo signal from the high-pass filter stage 24 is applied via conductor 30 and a coupling resistor 97, to the inverting input of an operational amplifier U3-A. It along with diodes 98 and 100, functions as a half-wave rectifier for the negative part of the excursion of the signal on line 30. A voltage divider including resistors 102 and 104 connects an offset voltage, via resistor 106, to the same inverting input of the op amp U3-A. Thus, for a half-wave rectified output to appear on output terminal 108, the input signal, applied via conductor 30, must exceed the positive offset voltage which may, for example, be about 15 millivolts.

The signal on line 30 is also applied, via a coupling resistor 110, to the inverting input of a operational amplifier U3-B which, along with diodes 112 and 114 also functions as a half-wave rectifier, but with respect to positive-going excursions of the input signal. A voltage divider, including resistors 116 and 118, is coupled between a negative reference voltage (−15 mv) and ground. The voltage divider output is then coupled through resistor 120 to the inverting input of Op Amp U3-B as a negative offset.

The output from the half-wave rectifier stages U3-A and U3-B are fed to a summing amplifier via coupling resistors 121 and 123 and summed together at the inverting input of the summing amplifier U4-B. The resulting output appears at a junction point 122. To convert this signal to a differential output, it is applied, via coupling resistor 124, to an inverter circuit U4-A and the non-inverted version and the inverted version become available on lines 38 and 40 for application to the microphone channel of an existing PSG machine.

Figure 3:
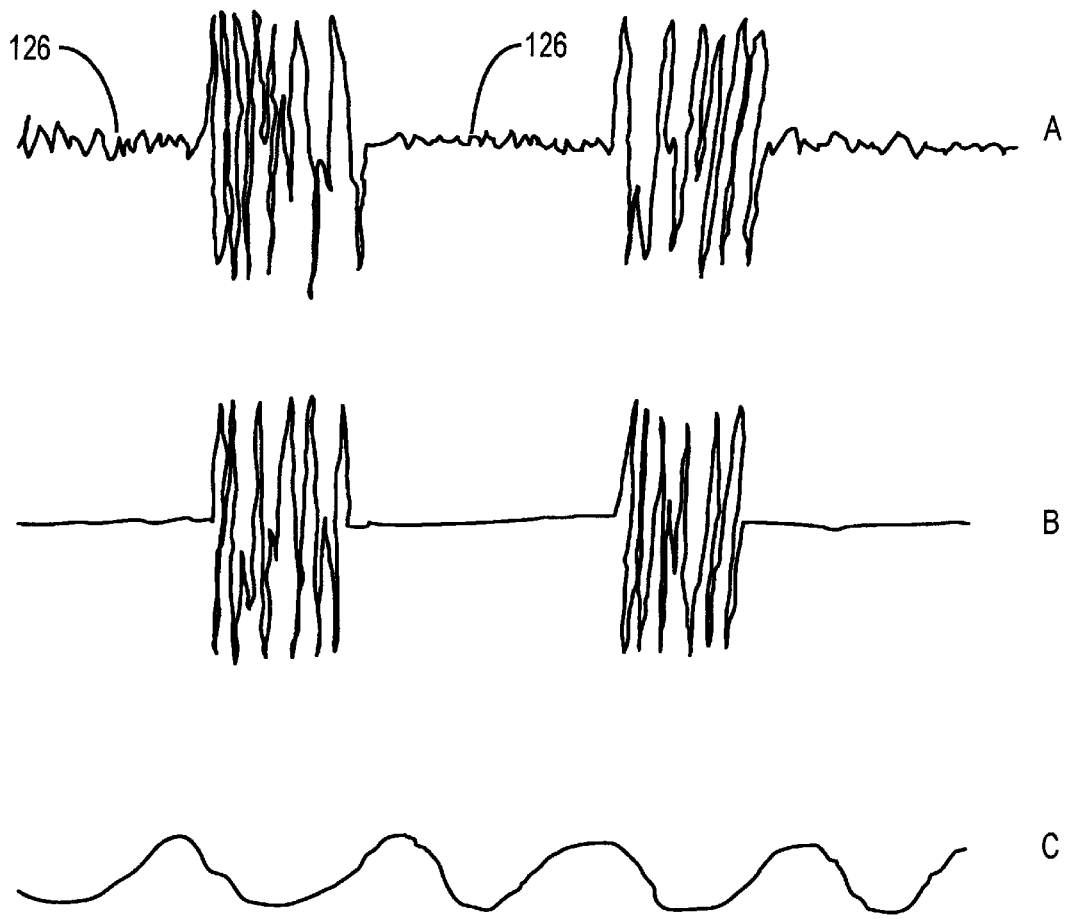
FIG. 3 are waveforms helpful in explaining the operation of the adapter module of the present invention.

Referring to the waveforms shown on FIG. 3, waveform A is representative of the amplified and high-pass filtered signal appearing on line 30 in FIGS. 1 and 2. The presence of baseline noise as at 126 is deemed objectionable by some and, as explained, the adapter unit 10 functions to eliminate that baseline noise. Waveform B is representative of the snore output signal appearing across the differential output lines 38 and 40 in FIGS. I and 2. The waveform of C in FIG. 3 is representative of the signal appearing on line 28 in the drawings of FIGS. 1 and 2.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself

What is claimed is:

1. An adapter for interfacing a pyro/piezo sensor to a PSG machine comprising:
    (a) an input amplifier having a pair of input terminals adapted to be coupled to said pyro/piezo sensor, an output terminal and a predetermined gain factor by which a sensor output signal is amplified;
    (b) a filter circuit connected to the output terminal of the differential input amplifier for separating a pyro component of the sensor output signal from a piezo component of the sensor output signal;
    (c) a dead band circuit coupled to an output of the filter circuit for removing baseline noise from the piezo component of the sensor output signal;
    (d) an output driver circuit coupled to an output of the dead band circuit adapted to provide a differential output signal to a PSG machine; and
    (e) the filter circuit adapted to provide the pyro component of the sensor output signal to the PSG machine.

2. The adapter of claim 1 wherein the predetermined gain factor of the differential input amplifier is in a range of from 2 to 10.

3. The adapter of claim 1 wherein the filter circuit comprises a low-pass filter for selectively passing the pyro component of the sensor output signal to a PSG machine and high-pass filter for passing the piezo component of the sensor output signal to the dead band circuit.

4. The adapter of claim 3 wherein the low-pass filter has a cut-off frequency of about 0.8 Hz and the high-pass filter has a cut-off frequency of about 20 Hz.

5. The adapter of claim 3 whereon the dead band circuit comprises first and second half-wave rectifier stages, each coupled to receive the piezo component passed by the high-pass filter and a predetermined reference voltage as an off-set, whereby only signal excursions of the piezo component of the sensor output signal exceeding the predetermined reference voltage are fed to the output driver.

6. The adapter of claim 5 wherein the first half-wave rectifier stage operates with a positive reference voltage and the second half-wave rectifier stage operates with a negative reference voltage.

7. The adapter of claim 5 wherein the output driver comprises a summing amplifier having an input coupled to receive output signals from the first and second half-wave rectifier stages and an output, said output of the summing amplifier connected as an input to an inverting amplifier.

* * * * *